United States Patent [19]

Wilke et al.

[11] Patent Number: 4,939,089

[45] Date of Patent: Jul. 3, 1990

[54] PROCESS FOR THE PREPARATION OF FESTUCLAVINE

[75] Inventors: Detlef Wilke, Wennigsen; Alfred Weber, Berlin, both of Fed. Rep. of Germany

[73] Assignee: Schering Aktiengesellschaft, Berlin and Bergkamen, Fed. Rep. of Germany

[21] Appl. No.: 842,110

[22] PCT Filed: May 30, 1985

[86] PCT No.: PCT/DE85/00189

§ 371 Date: Feb. 3, 1986

§ 102(e) Date: Feb. 3, 1986

[87] PCT Pub. No.: WO85/05634

PCT Pub. Date: Dec. 19, 1985

[30] Foreign Application Priority Data

Jun. 1, 1984 [DE] Fed. Rep. of Germany ....... 3420955

[51] Int. Cl.$^5$ .......................... C12P 17/18; C12N 1/14
[52] U.S. Cl. ........................ 435/49; 435/254; 435/911

[58] Field of Search ............... 435/119, 911, 171, 118, 435/254

[56] References Cited

PUBLICATIONS

Tscherter et al., *Helvetica Chimica Acta*, vol. 57, 1974, pp. 113–121.
Singh et al., *Indian J. Exp. Biol.*, vol. 15, pp. 585–586, 1977.
Sanardhanan et al., *Folia Microbiol.*, vol. 27, pp. 121–125, 1982.
Floss, H., *Tetrahedron*, vol. 32, pp. 873–912, 1976.
"The Merck Index", 10th Ed., p. 806, (1983).

*Primary Examiner*—Elizabeth C. Weimar
*Assistant Examiner*—Irene Marx
*Attorney, Agent, or Firm*—Millen, White & Zelano

[57] ABSTRACT

A process is claimed for the preparation of festuclavine, characterized by cultivating the microorganism *Claviceps paspali* 2838 and isolating the thus-formed festuclavine after termination of fermentation.

2 Claims, No Drawings

PROCESS FOR THE PREPARATION OF FESTUCLAVINE

The invention relates to the process characterized in the claims.

Festuclavine (6,8-dimethylergoline) is, as is known, a precursor for the biosynthesis of pharmacologically active ergot alkaloids and can be utilized, inter alia, for the production of pharmacologically effective N$_f$-alkyl-4,8-dimethylergolines. (CSSR Patent 189,458, referred to in C.A. 96 : 143148x, 1982.) However, according to the methods known heretofore, it is obtained by fermentative process only in a mixture with other ergot alkaloids. Consequently, its preparation and isolation are very expensive.

It has now been discovered that a fungal strain *Claviceps paspali* excretes festuclavine in high yields and practically free of other ergot alkaloids into the culture medium. This strain, *Claviceps paspali*, was isolated from an ergot of a type of grass of the genus *Paspalum*, growing wild in Argentina. This strain bears the internal designation SCHERING, MBCE 12426 and has been placed in the German collection for microorganisms under number DSM 2838. The strain forms shallow, rapidly growing colonies consisting of hyphae, conidia, and short, thickened and strongly vacuolated cells on agar media with glucose or sucrose as the carbon source and asparagine, ammonium succinate or complex nitrogen sources, such as peptone.

The hyphae have a diameter of 4–5 μm. The conidia are oval and have a width of 6–10 μm and a length of 10–20 μm. The colonies are grey-white, compact, and exhibit a lichen-like wrinkled surface and an irregularly fringed edge. The diameter of the colonies, after a cultivating period of 10 days, is 1–2 cm and, after a cultivating time of 35 days, 4–5 cm.

The process of this invention is performed under conditions usually employed for incubation of fungal cultures for metabolic synthesis. Thus, first a determination is made in generally customary preliminary tests to find the most favorable fermentation conditions, such as, for example, the choice of the most favorable nutrient medium, of the technical conditions, such as temperature, aeration, pH value, and of the optimum time periods for germination and for the development of the microorganism.

A suitable carbon source for the fermentation medium can be, for example, glucose or sucrose. Inter alia, asparagine, ammonium succinate or complex compounds, such as peptone, serve as the nitrogen source. The medium furthermore contains the required growth promoters (e.g. yeast extract) and mineral substances (potassium, magnesium, calcium, iron, and zinc cations, as well as sulfate, phosphate, nitrate, and chloride anions) in the usually employed concentration.

Fermentation can take place in one or two stages; in this connection, the medium employed for the subculture can be identical to that of the main culture or can be different therefrom.

At the beginning of fermentation, the pH of the medium is preferably set to be in a range from 4 to 6. The incubating temperature ranges from about 10° to 35° C, preferably from 20° to 30° C. The culturing conditions are strictly aerobic. The optimum fermentation period is determined in the usual way by analysis of the thus-formed festuclavine.

After fermentation has taken place, the thus-formed festuclavine is isolated conventionally, for example by extracting the fermentation batches with an organic solvent immiscible with water, such as ethyl acetate, methyl isobutyl ketone, dichloromethane, chloroform, or tetrachloroethane, concentration of the extracts, and purification of the resultant crude product by chromatography and/or crystallization.

The examples set forth below serve for an explanation of the process of this invention.

EXAMPLE 1

*Claviceps paspali* DSM 2838 is grown on a nutrient medium containing the following components:

Sucrose (100 g/l), asparagine (10 g/l), yeast extract (0.1 g/l), potassium dihydrogen phosphate (250 mg/l), magnesium sulfate heptahydrate (250 mg/l), potassium chloride (120 mg/l), calcium nitrate tetrahydrate (1 g/l), iron sulfate heptahydrate (20 mg/l), zinc sulfate heptahydrate (15 mg/l), agar (18 g/l). The nutrient medium is set at pH 5.1. The incubation culture is stored for 5–20 days at 30° C. in an incubator.

A piece of mycelium of a size of about 1 cm$^2$ is comminuted by means of an 'Ultra Turrax' mixer under sterile conditions in 5 ml of physiological sodium chloride solution and used for inoculating 50 ml of a subculture containing sucrose (100 g/l), peptone (20 g/l), potassium dihydrogen phosphate (1 g/l), magnesium sulfate heptahydrate (250 mg/l) provided in a 500 ml Erlenmeyer flask, and cultivated on a circular vibrator for 4 days at 24° C. and 220 rpm.

5 ml of the thus-obtained subculture is transferred into 50 ml of a medium containing sucrose (100 g/l), asparagine (10 g/l), yeast extract (0.1 g/l), potassium dihydrogen phosphate (250 mg/l), magnesium sulfate heptahydrate (250 mg/l), potassium chloride (120 mg/l), calcium nitrate tetrahydrate (1 g/l), iron sulfate heptahydrate (20 mg/l), and zinc sulfate (15 mg/l) —adjusted to pH 5.1 —present in a 500 ml Erlenmeyer flask, and shaken for 7 days at 24° C. on a circular vibrator at 240 rpm.

The culture medium is then removed by filtration, and the content of festuclavine is determined by photometry using the van Urk reaction (Mikrochim. Acta, 619–630, 1959). The concentration of the culture filtrate is 2.28 g/l.

EXAMPLE 2

Under the conditions of Example 1, but after exchanging the subculture medium and the main culture medium with each other, 2.07 g per liter of festuclavine is obtained in the medium of the main culture after a cultivating period of 9 days.

We claim:

1. A process for the preparation of festuclavine, characterized by cultivating the microorganism *Claviceps paspali DSM* 2838 and isolating the thus-formed festuclavine after termination of fermentation.

2. A process of claim 1, further comprising converting the thus-produced festuclavine to a pharmacologically active ergot alkaloid.

* * * * *